United States Patent
Azar

(10) Patent No.: US 7,229,476 B2
(45) Date of Patent: Jun. 12, 2007

(54) INTRAOCULAR LENS POSITIONING

(75) Inventor: Dimitri T. Azar, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 10/847,251

(22) Filed: May 17, 2004

(65) Prior Publication Data
US 2005/0256571 A1    Nov. 17, 2005

(51) Int. Cl.
*A61F 2/16* (2006.01)
(52) U.S. Cl. .................... 623/6.26; 623/6.36; 623/6.37
(58) Field of Classification Search ............... 623/6.22, 623/6.37, 6.23, 6.26, 6.32, 6.33, 6.34, 6.36
See application file for complete search history.

(56) References Cited

U.S. PATENT DOCUMENTS

| 4,190,330 | A | 2/1980 | Berreman |
| 4,230,942 | A | 10/1980 | Stauffer |
| 4,309,603 | A | 1/1982 | Stauffer |
| 4,466,703 | A | 8/1984 | Nishimoto |
| 4,601,545 | A | 7/1986 | Kern |
| 4,787,903 | A | 11/1988 | Grendahl |
| 5,182,585 | A | 1/1993 | Stoner |
| 5,359,444 | A | 10/1994 | Piosenka et al. |
| 5,593,437 | A | 1/1997 | Arita et al. |
| 5,800,530 | A | 9/1998 | Rizzo, III |
| 6,638,304 | B2 | 10/2003 | Azar |

FOREIGN PATENT DOCUMENTS

EP    0 162 573 A2 *   11/1985

* cited by examiner

*Primary Examiner*—David H. Willse
(74) *Attorney, Agent, or Firm*—Fish & Richardson P.C.

(57) ABSTRACT

An optical element is adapted for implantation into a vitreous chamber of an eye, and a suspension system is configured to position a portion of the optical element to intersect a visual axis of an eye.

21 Claims, 7 Drawing Sheets

INTRAOCULAR LENS POSITIONING

FIELD OF INVENTION

The invention relates to intraocular lens positioning.

BACKGROUND

In the course of daily life, one typically regards objects located at different distances from the eye. To selectively focus on such objects, the focal length of the eye's lens must change. In a healthy eye, this is achieved through the contraction of a ciliary muscle that is mechanically coupled to the lens. To the extent that the ciliary muscle contracts, it deforms the lens. This deformation changes the focal length of the lens. By selectively deforming the lens in this manner, it becomes possible to focus on objects that are at different distances from the eye. This process of selectively focusing on objects at different distances is referred to as "accommodation."

As a person ages, the lens loses plasticity. As a result, it becomes increasingly difficult to deform the lens sufficiently to focus on objects at different distances. This condition is known as presbyopia. Refractive errors caused by such conditions as hyperopia, myopia, as well as aberrations due to irregularities in the eye (e.g., in the cornea or in the natural crystalline lens) can also cause problems in one's ability to focus on an object. To compensate for this loss of function, it is useful to provide different optical corrections for focusing on objects at different distances. Some restoration of focusing ability for some distances can be provided by spectacles or contact lenses. There are also a variety of disorders that degrade the ability of the eye to function properly. These include vitreoretinal disorders, lenticular disorders, corneal disorders, and glaucomatous states. Some treatments to some of these types of disorders involve surgical intervention. For example, a common disorder involves progressive clouding of the natural crystalline lens resulting in the formation of what is referred to as a cataract. A common practice used to treat a cataract is surgically removing the cataractous natural crystalline lens and implanting (in the "aphakic" patient) an artificial intraocular lens into the empty lensbag to replace the natural crystalline lens. After cataract surgery, the corneal incision (and/or limbal and scleral incisions) can potentially induce optical aberrations due to altered corneal curvature and topography. Intraocular lenses can also be used for a "phakic" patient who still has a natural crystalline lens. One or more lenses are placed in front of the natural crystalline lens (e.g., in the anterior or posterior chamber) to provide added focusing power.

SUMMARY

The invention features an intravitreal optical element positioned within the vitreous chamber of a patient's eye.

In one aspect, the invention features an apparatus including an optical element adapted for implantation into a vitreous chamber of an eye, and a suspension system configured to position a portion of the optical element to intersect a visual axis of an eye.

In another aspect, the invention features a method including providing an optical element for implantation into a vitreous chamber of an eye, and providing a suspension system coupled to the optical element for positioning the optical element with a portion of the optical element intersecting a visual axis of an eye.

Embodiments of the invention may include one or more of the following features.

The suspension system includes an attachment structure attached to the optical element and configured for attachment to a portion of an eye.

The suspension system includes an electromagnetic suspension system including a first electromagnetic element attached to the optical element, and a second electromagnetic element configured for attachment to a portion of an eye.

The optical element includes a first lens. The optical element may also include a second lens adapted for implantation into the anterior chamber, the posterior chamber, the lens-bag, or the cornea. A second lens may be in optical communication with the first lens.

The optical element has an adjustable focal length.

A haptic sensor is coupled to the optical element for sensing a stimulus provided by an anatomical structure of the eye. The haptic sensor is configured to generate, from the stimulus, a signal that controls the focal length of the optical element.

The optical element is configured to switch among a plurality of positions. In a first of the plurality of positions, the optical element is positioned to center a focused image onto the fovea of the eye. In a second of the plurality of positions, the optical element is positioned to center a focused image onto the optic nerve head of the eye.

The optical element includes a prism in optical communication with the optical element that is configured to switch among a plurality of positions. In a first of the plurality of positions, the prism is positioned to center a focused image onto the fovea of the eye. In a second of the plurality of positions, the prism is positioned to center a focused image onto the optic nerve head of the eye.

The optical element is configured to have a characteristic function associated with refraction therethrough, the characteristic function being selected to compensate for pre-existing aberration in the eye.

As used herein, "visual axis" means any line passing through the pupil of an eye and passing through any portion of the retina.

As used herein, "vitreous chamber" means a chamber of an eye bounded by the retina and the lens-bag, or, in the absence of a lens-bag (e.g., after cataract surgery), bounded by the retina and the ciliary body.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will become apparent from the following description, and from the claims.

DESCRIPTION

An intravitreal optical element implanted within the vitreous chamber of an eye provides features that are useful for correcting various impairments and disorders, as well as for enabling greater control over an image focused onto the retina. Implantation within the vitreous chamber avoids complications arising from disturbing parts of the eye in front of the crystalline lens, such as the anterior chamber, iris, or corneal structures.

Figure 1A:
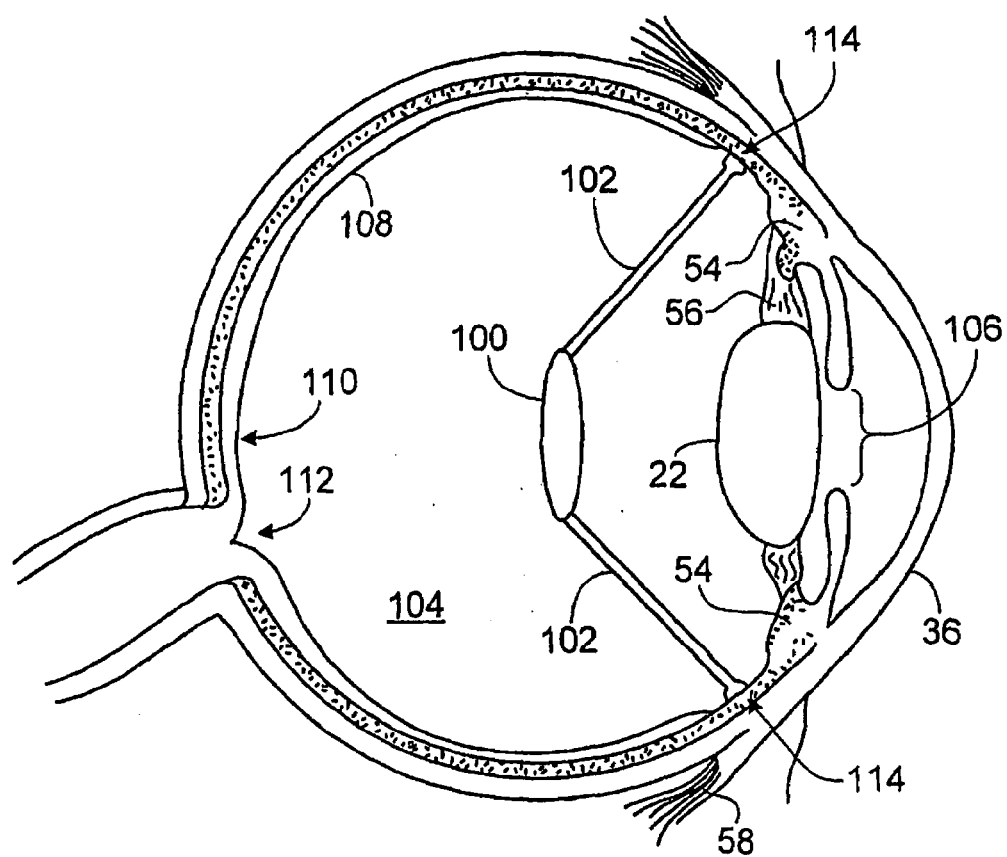
FIG. 1A–1B show an intravitreal optical element implanted in an eye.

FIG. 1A shows an intravitreal optical element 100 implanted in an eye of a human patient and suspended by a mechanical suspension system. An attachment structure 102 secures the intravitreal optical element 100 within the vitreous chamber 104 of the eye. The intravitreal optical element 100 focuses light entering the eye through the pupil 106 onto the retina 108. The attachment structure 102 maintains the intravitreal optical element 100 in a stable position with respect to the pupil 106 and the retina 108. The intravitreal optical element 100 can include a focusing element such as a single lens, multiple lenses in a telescopic arrangement, or a mosaic of multiple microlenses or lenslets.

Figure 1B:
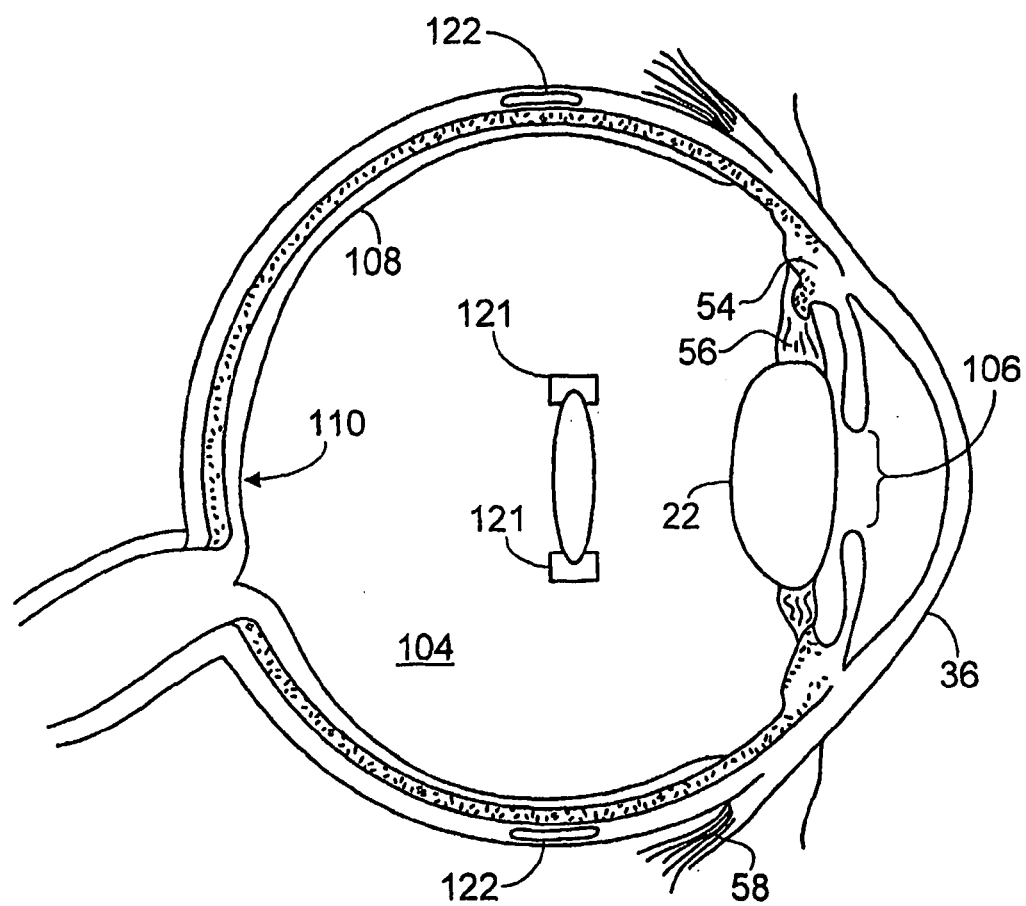

FIG. 1B shows an intravitreal optical element 100 implanted in an eye of a human patient and suspended by an electromagnetic suspension system. The electromagnetic suspension system includes a first electromagnetic element 121 (e.g., a ferromagnetic material) attached as a ring around the intravitreal optical element 100, and a second electromagnetic element 122 (eg., one or more electromagnets) implanted in the eye in a ring around the first electromagnetic element 121. The optical element 100 is suspended in the vitreous chamber by electromagnetic forces between the electromagnetic elements (e.g., magnetic levitation). Optionally, the electromagnetic suspension system can include a feedback system to stabilize the position of the first electromagnetic element 121 and the optical element 100 to which it is attached. For example, one or more Hall effect sensors, which operate by producing a voltage that is proportional to the strength of a magnetic field at its location, can be used to sense the position of the first electromagnetic element 121. Error signals can then be provided as current supplied to electromagnets in the second electromagnetic element 122 to control the position of the first electromagnetic element 121.

In some embodiments, the focal length of the intravitreal optical element 100 is adjustable to provide accommodation, alone or in combination with either a natural crystalline lens or an artificial intraocular lens within the lens-bag 22. When an object-of-regard is in focus, the image of the object-of-regard is focused at the retina 108. A haptic sensor attached to the intravitreal optical element 100 and to an anatomical structure of the eye senses a stimulus from the eye, the stimulus indicating a distance to an object-of-regard. The haptic sensor uses a transducer to convert the stimulus from the eye into a focusing signal to be provided to the intravitreal optical element 100, as described in more detail below. The focal length of the intravitreal optical element 100 changes in response to the focusing signal provided by the haptic sensor to focus the image of the object-of-regard at the retina 108.

Figure 2:
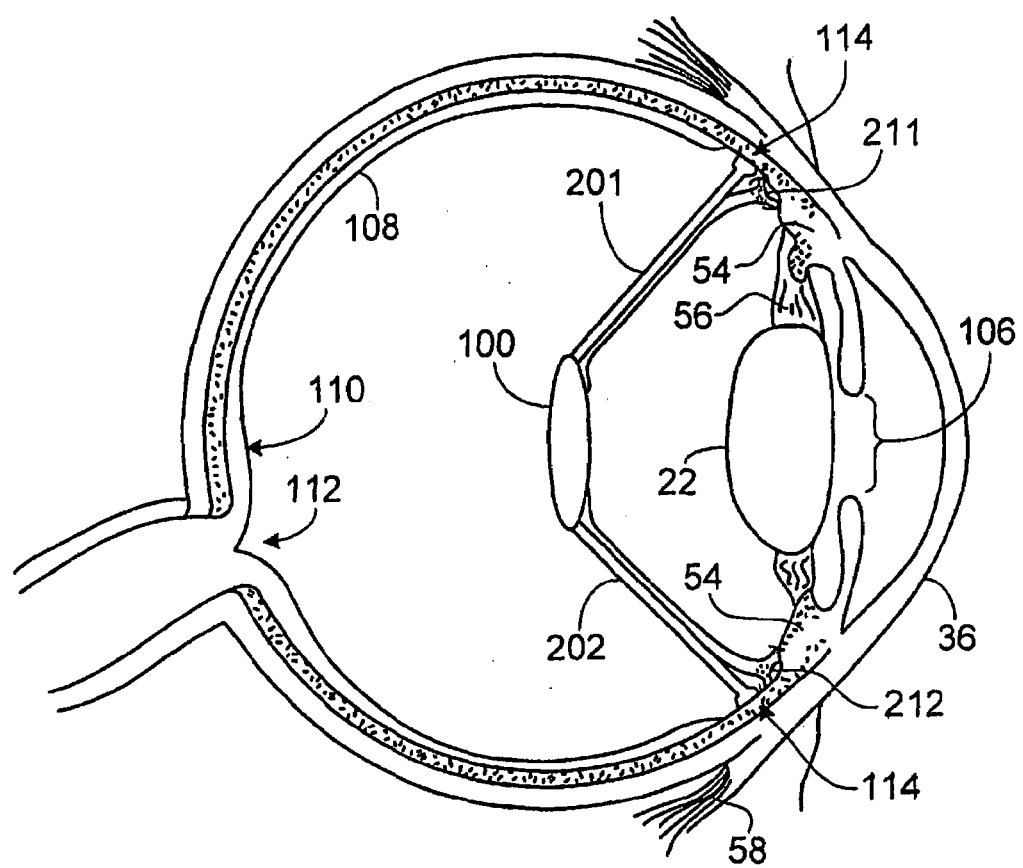
FIG. 2 shows an intravitreal optical element in an eye, with haptic sensors attached to the optical element and to the eye.

Referring to FIG. 2, in one embodiment, the attachment structure 102 has a first attachment arm 201 attached on a first side of the intravitreal optical element 100, and a second attachment arm 202 attached on a second side of the intravitreal optical element 100, the second side being opposite the first side. The attachment arms are composed of a material suitable for implantation in the eye, such as polypropylene, polyacrylamide, or polymethyl methacrylate, among others. The intravitreal optical element 100 receives a focusing signal from a first haptic sensor 211 attached to the first attachment arm 201 and a second haptic sensor 212 attached to the second attachment arm 202. Each haptic sensor detects a stimulus from the ciliary muscle 54.

Alternatively, other attachment structures can be used. For example, three or more attachment arms, or a single integral attachment structure with three or more points of attachment to the eye can be used. If the attachment structure applies pressure to three or more points in the eye, then the attachment structure may stay attached to the eye without being sutured in place.

Techniques for changing the focal length of the intravitreal optical element 100 include changing focusing power by changing the shape and/or index of refraction of material within the intravitreal optical element 100, or changing axial position (along a visual axis) of lenses in a telescopic arrangement. In one embodiment, the intravitreal optical element 100 includes a nematic liquid-crystal whose index of refraction varies in response to an applied electric field. In this case, each of the haptic sensors 211, 212 sends a signal to one or more electrodes in electrical communication with the nematic liquid-crystal. In addition to, or instead of, a change in index of refraction, the shape of a movable surface of the intravitreal optical element 100 changes (e.g., deforming the surface by changing a chemical or mechanical property) in response to the signal provided by the haptic sensor. A power source located in the eye supplies power to any components in the intravitreal optical element 100 that need power, as described in more detail below.

Implantation and Suspension

The intravitreal optical element 100 is inserted into the vitreous chamber 104 through an opening in the sclera. Space can be made for the intravitreal optical element 100 and the attachment structure 102 by performing a limited or extensive vitrectomy. A second scleral opening is used to insert an instrument 222 (FIG. 3) that can be used to help guide the intravitreal optical element 100 and the attachment structure 102 into place. Each of the attachment arms 201–202 is secured by suturing a portion of the arm to an anatomical structure of the eye (e.g., the pars plana 114). Alternatively, the ends of the attachment arms 201–202 can be passed through the scleral incision to be secured to the eye.

Figure 3:
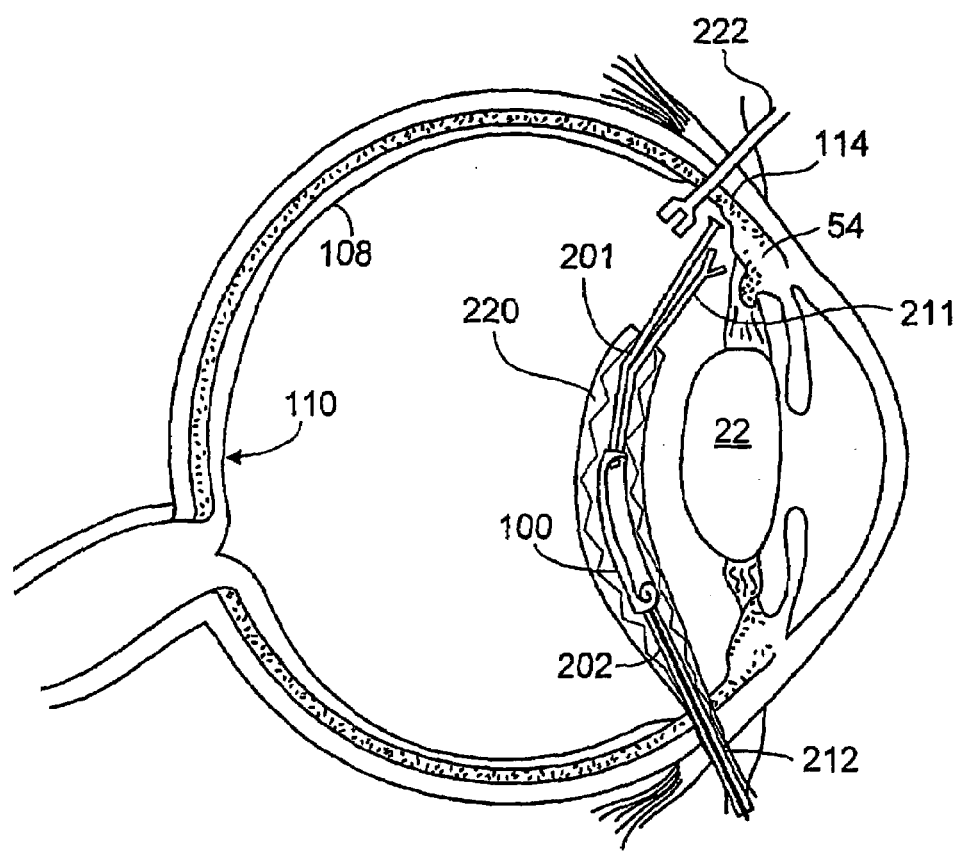
FIG. 3 shows an intravitreal optical element inside an injector tool (through a cutaway view) for insertion into an eye.

Referring to FIG. 3, an injector tool 220 can be used to for implanting the intravitreal optical element 100 with attachment arms 201–202 and haptic sensors 211–212. The intravitreal optical element 100 can be made of a flexible material such as polymethyl methacrylate (PMMA) or acrylic that can be folded and can spring back into an unfolded state. A surgeon folds the intravitreal optical element 100 and haptic sensors 211–212 and inserts them inside the injector tool 220. The surgeon then inserts the injector tool 220 into the scleral opening and retracts the injector tool 220 enough to release the first haptic sensor 211, which then unfolds. The injector tool 220 can be curved to avoid the lens-bag 22. The surgeon secures the first attachment arm 201 to the pars planal 14, and the first haptic sensor 211 to the ciliary muscle 54. The surgeon then retracts the injector tool 220, removing it from the eye and allowing the intravitreal optical element 100 and second haptic sensor 212 to unfold. The surgeon secures the second attachment arm 202 to the pars plan 114 and the second haptic sensor 212 to the ciliary muscle 54. The surgeon then positions the intravitreal optical element 100 to intersect the visual axis so that light passing through the center of the pupil 106 is focused on the fovea 110 near the center of the retina 108.

Other techniques for implanting the intravitreal optical element 100 include using larger incisions for more direct application, using other folding methods, or using a different number of attachment arms. When the intravitreal optical element 100 includes an electromagnetic suspension system, the surgeon inserts the intravitreal optical element 100 into the vitreous chamber and moves it into position to be stabilized by the electromagnetic suspension system.

Image Adjustment

The intravitreal optical element 100 focuses an image of an object-of-regard onto the retina 108. Various types of image adjustments can be made by adjusting components within the intravitreal optical element 100. For example, the size of the image on the retina can be changed while keeping the image focused on the retina 108 by using a telescopic lens arrangement having two or more lenses. One of the lenses of a telescope is within the intravitreal optical element 100. Other lenses of the telescope can be in any of a variety of locations such as within the intravitreal optical element 100, in the lens-bag 22, in the posterior chamber 24, in the anterior chamber 34, in the cornea 36, or outside the eye (e.g., as contact lenses or spectacles). The lens within the intravitreal optical element 100 can be a positive lens or a negative lens. For example, as part of a Galilean telescope, a negative lens within the intravitreal optical element can have an index that is larger than the index of the vitreous fluid and a concave shape, or an index that is smaller than the index of the vitreous fluid (e.g., an air-filled lens) and a convex shape. Some arrangements (e.g., two positive lenses) may include an image inverter (e.g., a prism) intercepting a visual axis to provide an image on the retina 108 that has a "correct" orientation so that a patient perceives a scene properly (i.e., not inverted). (In some cases a patient may adapt to an incorrect orientation of an image on the retina 108.)

The combined effect of the lenses in such a telescope is to provide magnification (e.g., 10x) or demagnification (e.g., 0.1x) of the image of an object-of-regard with respect to a default image size. The size of the image is changed without changing the position of the focus (at the retina 108) by changing the power of one or more of the lenses in the telescope and/or the axial position (along a visual axis) of one or more of the lenses in the telescope. Since one of the lenses of the telescope (i.e., the lens in the intravitreal optical element 100) is located in the vitreous chamber 104, the telescope can have a large distance between lenses (e.g., larger than about 10 mm). A larger distance between lenses of the telescope enables higher magnification to be achieved and/or lower index materials to be used.

Figure 4:
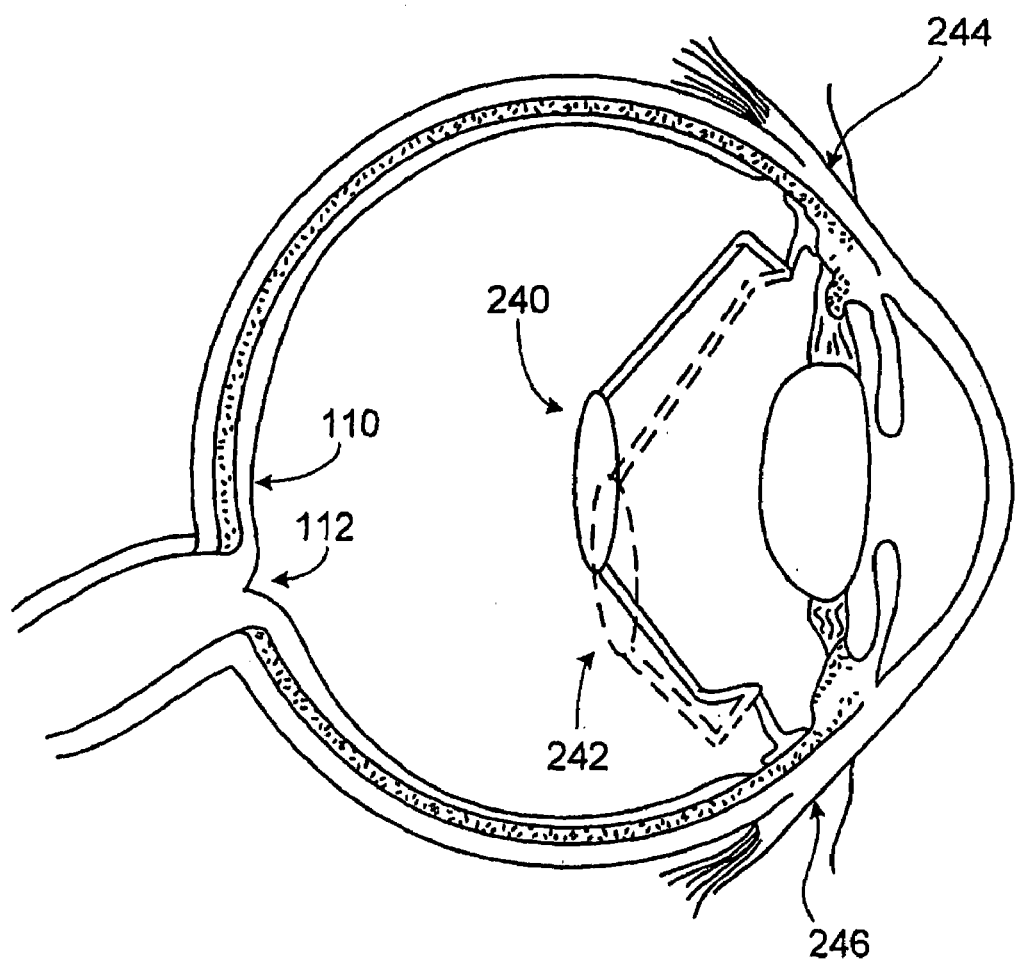
FIG. 4 shows an intravitreal optical element in an eye, with an on/off position switch for the optical element.
Figure 5:
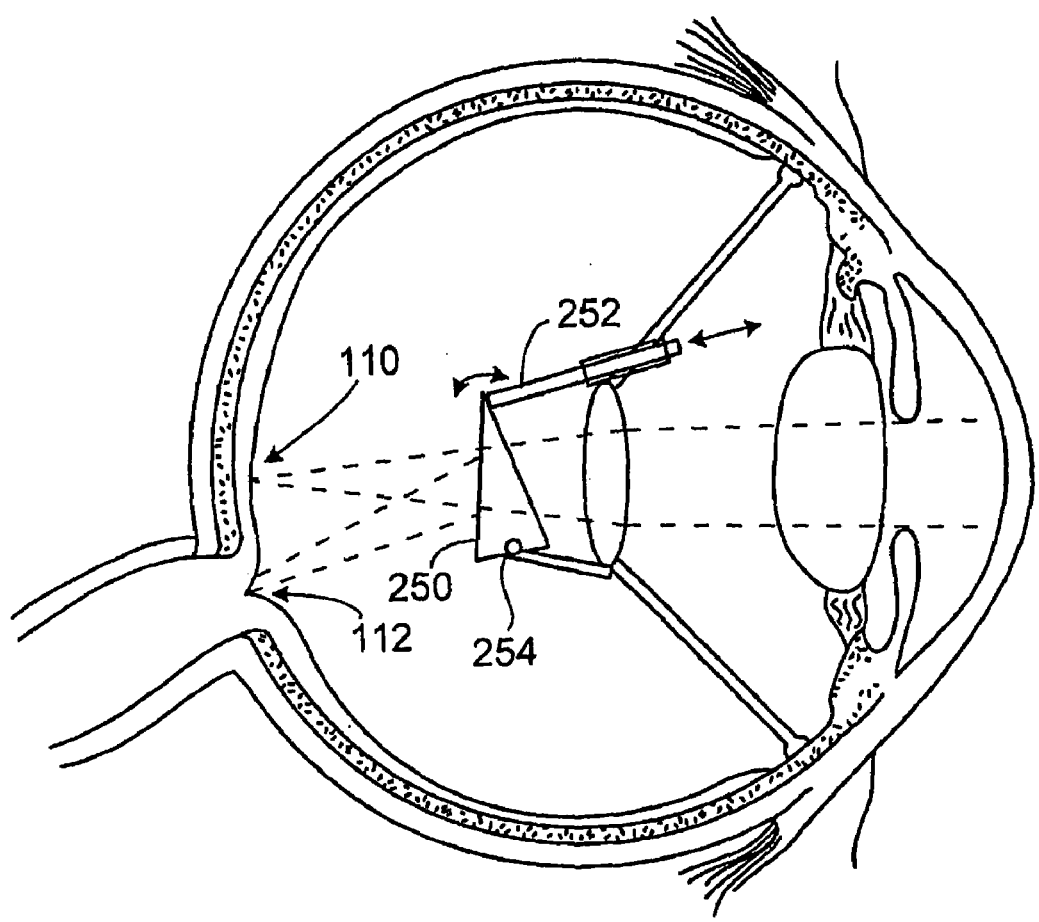
FIG. 5 shows an intravitreal optical element in an eye, with an on/off position prism for the optical element.

Another type of adjustment that can be made is to "turn off" an image. To do so, the position of the intravitreal optical element 100 is shifted such that the image is no longer centered on the fovea 110, but is instead centered on the optic nerve head 112 (the "blind spot"). In one embodiment, illustrated in FIG. 4, the intravitreal optical element is 100 switches between an "on" position 240 and an "off" position 242. A pressure sensitive switching mechanism is used to switch the intravitreal optical element 100 between the "on" 240 and "off" 242 positions. External pressure applied in a spot 244 on one side of the eye switches from the "on" position 240 to the "off" position 242, and external pressure applied in a spot 246 on another side of the eye switches from the "off" position 242 to the "on" position 240. In another embodiment, illustrated in FIG. 5, a prism 250 is used to switch an image between an "on" position focused on the fovea 110 and an "off" position focused on the optic nerve head 112. The image is switched by action of a sliding arm 252 that tilts the prism 250 about a pivot point 254.

In some cases, the intravitreal optical element 100 restores a patient's ability to focus. In other cases, the intravitreal optical element 100 provides visual abilities that a patient may wish to adjust or deactivate.

In some embodiments, the intravitreal optical element 100 can be switched out of the path of a visual axis of the eye. For example, if the intravitreal optical element 100 includes a lens that is part of a telescope, the magnification provided by the telescope can be turned off or adjusted using a switching mechanism to control any of the lenses of the telescope. Alternatively, the effect of the intravitreal optical element 100 can be switched off by changing the index of material within the intravitreal optical element (e.g., of a nematic liquid-crystal) to match the index of the vitreous fluid.

Wavefront Aberration Correction

The intravitreal optical element 100 can also correct for wavefront aberrations present in a patient's eye (e.g., due to abnormalities in the cornea, the natural crystalline lens, or the ocular media). A wavefront of light passing through the intravitreal optical element 100 will be altered in a way that can be described by a characteristic function associated with refraction through the intravitreal optical element 100. The characteristic function of an intravitreal optical element 100 can be estimated from knowledge of the optical path length traversed by any ray of light passing through any portion of the element. For an intravitreal optical element 100 comprised of various media having various surfaces, the optical path length can be determined from the index of refraction within the various media and the shapes of their corresponding surfaces. This type of analysis can also be used to design and construct an intravitreal optical element 100 having a desired characteristic function. Upon measuring any pre-existing aberrations in a patient's eye, one can design the intravitreal optical element 100 to have a characteristic function that compensates for the effects of pre-existing aberrations. As a result, the intravitreal optical element 100 reduces the perceived effect of any residual aberrations.

To provide adjustable correction for wavefront aberrations, a change in the shape, or index of refraction, of material within the intravitreal optical element 100 is made a function of more than one spatial variable. By providing a plurality of actuating elements coupled to different local regions of the intravitreal optical element 100 (e.g., distributed in a polar grid or a rectilinear grid), the optical path length through the intravitreal optical element 100 can be varied at those local regions. For example, electrodes can apply a field to change the local refractive index, or mechanical actuators can apply force to deform local regions of a reflecting or refracting surface.

Haptic Sensor

In a normal eye, contraction of a ciliary muscle 54 is transmitted to the natural crystalline lens inside the lens-bag 22 by zonules 56 extending between the ciliary muscle 54 and the lens-bag 22. When an object-of-regard is nearby, the ciliary muscle 54 contracts, thereby deforming the natural crystalline lens so as to bring an image of the object into focus on the retina. When the object-of-regard is distant, the ciliary muscle 54 relaxes, thereby restoring the natural crystalline lens to a shape that brings distant objects into focus on the retina 108. The activity of the ciliary muscle 54 thus provides an indication of the distance to an object-of-regard.

The haptic sensors 211, 212 include a transducer for detecting a stimulus (e.g., contraction of the ciliary muscle 54). In one implementation, the haptic sensor can include a pressure transducer that detects the mechanical activity of the ciliary muscle 54. A pressure transducer coupled to the ciliary muscle 54 can be a piezoelectric device that deforms, and hence generates a voltage, in response to contraction of the ciliary muscle 54. In another implementation, the haptic sensor can include an electromyograph for detecting electrical activity within the ciliary muscle 54.

As noted above, the activity of the ciliary muscle 54 is transmitted to the natural crystalline lens by zonules 56 extending between the ciliary muscle 54 and the lens-bag 22. Both the tension in the zonules 56 and the resulting mechanical disturbance of the lens-bag 22 can be also be used as indicators of the distance to the object-of-regard. In recognition of this, the haptic sensor can also include a tension measuring transducer in communication with the zonules 56 or a motion sensing transducer in communication with the lens-bag 22. These sensors can likewise be piezoelectric devices that generate a voltage in response to mechanical stimuli.

The activity of the rectus muscles 58 can also be used to infer the distance to an object-of-regard. For example, a contraction of the rectus muscles 58 that would cause the eye to converge medially suggests that the object-of-regard is nearby, whereas relaxation of the rectus muscles 58 that would cause the eye to gaze forward suggests that the object-of-regard is distant. The haptic sensor can thus include a transducer that responds to either mechanical motion of the rectus muscles 58 or to the electrical activity that triggers that mechanical motion.

Power Source

Figure 6:
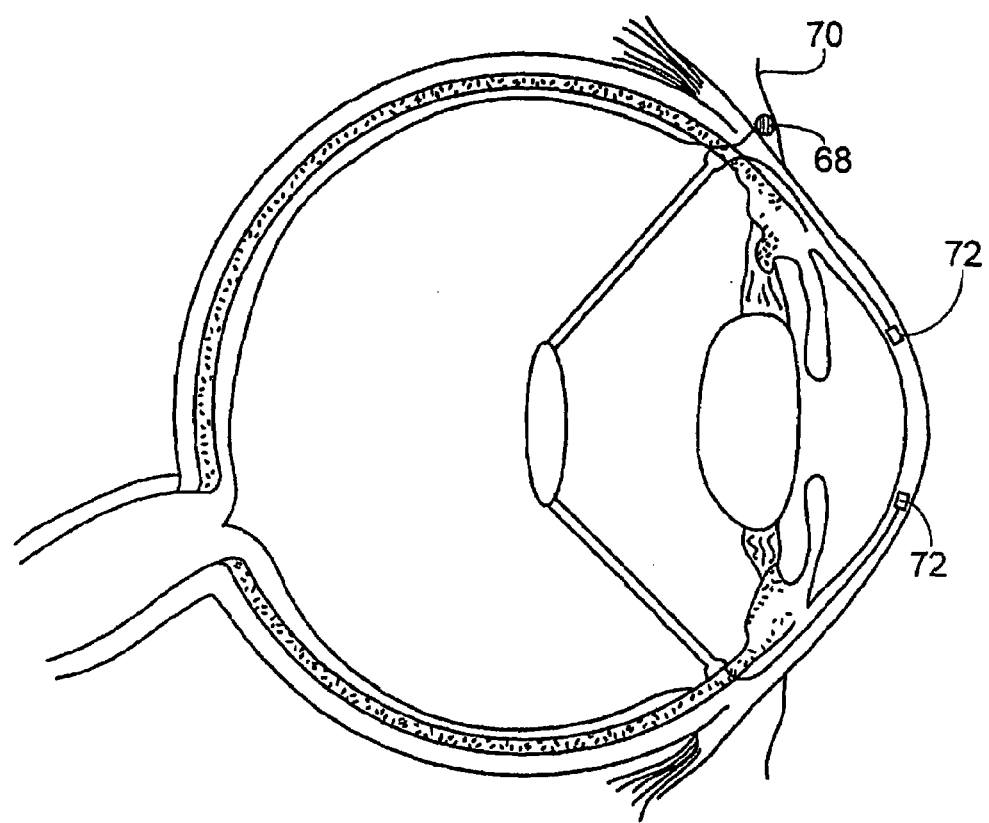
FIG. 6 shows possible locations in an eye for a power source.

As noted above, components within the intravitreal optical element 100 obtain power from an electrical power source in the eye in electrical communication with the intravitreal optical element 100. FIG. 6 illustrates possible locations in the eye for a power source. In one embodiment, the power source can be an implanted battery 68. The battery 68 can be implanted in any convenient location, such as under the conjunctiva 70 in the Therron's capsule, or within the sclera. Unless it is rechargeable in situ, such a power source will periodically require replacement.

In another embodiment, the power source is a photovoltaic cell 72 implanted in a portion of the eye that receives sufficient light to power the components that need power. The photovoltaic cell 72 is mounted on a peripheral portion of the intravitreal optical element 100 where it will receive adequate light without interfering excessively with vision. Alternatively, the photovoltaic cell is implanted within the cornea 36, where it will receive considerably more light.

When implanted into the cornea 36, a photovoltaic cell 72 formed into an annulus or a portion of an annulus centered at the center of the cornea 36 avoids excessive interference with the patient's vision while providing sufficient area for collection of light.

Power generated by such a photovoltaic cell 72 can also be used to recharge a battery 68, thereby enabling the intravitreal optical element 100 to operate under low-light conditions. The use of a photovoltaic cell 72 as a power source eliminates the need for the patient to undergo the invasive procedure of replacing an implanted battery 68.

It is to be understood that while the invention has been described in conjunction with the detailed description thereof, the foregoing description is intended to illustrate and not limit the scope of the invention, which is defined by the scope of the appended claims.

What is claimed is:

1. An apparatus comprising:
   an optical element adapted for implantation into a vitreous chamber of an eye; and
   a suspension system configured to position a portion of the optical element to switch between a first position in which a ray of light passing through a portion of the pupil is directed onto the fovea of the eye, and a second position in which the ray of light is directed onto the optic nerve head of the eye.

2. The apparatus of claim 1 wherein the optical element comprises a first lens.

3. The apparatus of claim 2 further comprising a second lens adapted for implantation into a location in an eye, the location being selected the group consisting of:
   the anterior chamber;
   the posterior chamber;
   the lens-bag; and
   the cornea.

4. The apparatus of claim 2 further comprising a second lens in optical communication with the first lens.

5. The apparatus of claim 1 wherein the optical element has an adjustable focal length.

6. The apparatus of claim 5 further comprising a haptic sensor coupled to the optical element for sensing a stimulus provided by an anatomical structure of the eye.

7. The apparatus of claim 6 wherein the haptic sensor is configured to generate, from the stimulus, a signal that controls the focal length of the optical element.

8. The apparatus of claim 1 wherein the optical element includes a prism in optical communication with the optical element, the prism being configured to switch between the first postion and the second position.

9. The apparatus of claim 1 wherein the optical element is configured to have a characteristic function associated with refraction therethrough, characteristic function being selected to compensate for pre-existlug aberration in the eye.

10. The apparatus of claim 1, wherein the suspension system is configured to switch in response to applied pressure.

11. The apparatus of claim 1 wherein the suspension system comprises an attachment structure attached to the optical element and configured for attachment to a portion of an eye.

12. The apparatus of claim 1 wherein the suspension system comprises an electromagnetic suspension system comprising:
   a first electromagnetic element attached to the optical element; and
   a second electromagnetic element configured for attachment to a portion of an eye.

13. The apparatus of claim 1, wherein the portion of the pupil comprises the center of the pupil.

14. The apparatus of claim 1, wherein the portion of the pupil comprises an edge of the pupil.

15. A method comprising:
   implanting an optical element into a vitreous chamber of an eye; and
   positioning the optical element so that a ray of light passing through a portion of the pupil is directed onto the fovea of the eye; and
   switching the postion of the optical element so that the ray of light is directed onto the optic nerve head of the eye.

16. The method of claim 15, wherein the optical element comprises a lens.

17. The method of claim 15, wherein switching comprises switching in response to applied pressure.

18. The method of claim 15, wherein implanting the optical element comprises attaching an attachment structure attached to the optical element to a portion of an eye.

19. The method of claim 15, wherein implanting the optical element comprises attaching:
   a first electromagnetic element to the optical element; and
   a second electromagnetic element to a portion of an eye.

20. The method of claim 15, wherein the portion of the pupil comprises the center of the pupil.

21. The method of claim 15, wherein the portion of the pupil comprises an edge of the pupil.

* * * * *